United States Patent
Brands et al.

(10) Patent No.: US 7,276,637 B2
(45) Date of Patent: Oct. 2, 2007

(54) SYNTHESIS OF CYCLOHEXANONE DERIVATIVES

(75) Inventors: Karel Marie Joseph Brands, Rahway, NJ (US); Antony John Davies, Broxbourne (GB); Paul Joseph Oakley, Bishops Stortford (GB); Jeremy Peter Scott, Harlow (GB); Duncan Edward Shaw, Bishops Stortford (GB); Martin Richard Teall, Bishops Stortford (GB)

(73) Assignees: Merck Sharp & Dohme Limited, Hoddesdon Hertfordshire (GB); Merck & Co., Inc., Rahway, NJ (US)

( * ) Notice: Subject to any disclaimer, the term of this patent is extended or adjusted under 35 U.S.C. 154(b) by 332 days.

(21) Appl. No.: 10/522,261

(22) PCT Filed: Jul. 30, 2003

(86) PCT No.: PCT/GB03/03224

§ 371 (c)(1),
(2), (4) Date: Jan. 25, 2005

(87) PCT Pub. No.: WO2004/013090

PCT Pub. Date: Feb. 12, 2004

(65) Prior Publication Data

US 2005/0222456 A1    Oct. 6, 2005

(30) Foreign Application Priority Data

Aug. 2, 2002 (GB) ................................. 0218041.2

(51) Int. Cl.
*C07C 15/00* (2006.01)
(52) U.S. Cl. ..................................................... 585/407
(58) Field of Classification Search .................... None
See application file for complete search history.

(56) References Cited

FOREIGN PATENT DOCUMENTS

EP    1 122 234    8/2001
GB    WO 03/018543 A1 *  3/2003
WO    WO 02/081435    10/2002

OTHER PUBLICATIONS

Scott, J.P. et al. Tetrahedron Letters 2004, 45, 3345-3348.*
Y. Rao et al., "Diels-Alder Reactions of 1,1 Bis[benzenesulfonyl]ethene," Synthesis, 1984, pp. 757-758, XP002257838.
T. Gunda, "Mannich Reactions of Cephalosporin Sulphoxides and Sulphones with Imonium Salts. An Improved Synthesis of 2-Methylene-Cephalosporins," Synthetic Communications, vol. 22, No. 20, 1992, pp. 2979-2986, XP001091311.
R. R. Wroble et al., "A Synthesis of Alpha, Beta-Unsaturated Ketones from Alpha, Beta-Unsaturated Nitriles," J. Org. Chem., vol. 41, No. 17, 1976, pp. 2939-2940, XP002257839.
B. Ganem et al., "Unique Methodology for the Conjugate Reduction and Reductive Alkylation of Alpha, Beta-Unsaturated Carboxylic Esters," J. Org. Chem., vol. 40, No. 19, 1975, pp. 2846-2848, XP002257840.
"Houben-Weyl Methoden Der Organischen Chemie, Suppl. to 4th Edition, vol. E3", 1983, Georg Thieme Verlag, Stuttgart, De, XP002257841.
M. Petrzilka, "New Liquid Crystals: The Synthesis and Mesomorphic Properties of Nematic Alkenylsubstituted Cyanophenylcyclohexanes", Mol. Cryst. Liq. Cryst., vol. 131, 1985, pp. 109-123, XP001091310.

* cited by examiner

*Primary Examiner*—D. Margaret Seaman
*Assistant Examiner*—Nizal S. Chandrakumar
(74) *Attorney, Agent, or Firm*—John Todaro; William Krovatin

(57) ABSTRACT

A novel process for preparing cyclohexanone derivatives of formula (I)

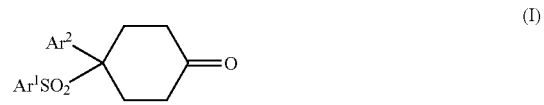

is described. The products are useful as gamma secretase inhibitors, or as intermediates in the synthesis of other gamma secretase inhibitors.

13 Claims, No Drawings

SYNTHESIS OF CYCLOHEXANONE DERIVATIVES

CROSS REFERENCE TO RELATED APPLICATIONS

This application is a U.S. National Phase application under 35 U.S.C. § 371 of PCT Application No. PCT/GB03/03224, filed Jul. 30, 2003, which claims priority under 35 U.S.C. § 119 from GB Application No. 0218041.2, filed Aug. 2, 2002.

This invention is in the field of synthetic organic chemistry, and in particular concerns a novel synthetic route to a particular class of 4,4-disubstituted cyclohexanones which have useful therapeutic properties, and which are key intermediates in the synthesis of further compounds having therapeutic properties.

As disclosed in our copending International Patent Application No. PCT/GB01/03741, filed 21 Aug. 2001, now published as WO 02/081435, a particular class of cyclohexane derivatives have been found to have activity as modulators of the processing of amyloid precursor protein (APP) by γ-secretase into the β-amyloid peptide. Since the secretion of β-amyloid is believed to play a primary role in the onset and progression of Alzheimer's disease, the said cyclohexane derivatives are useful in the treatment and/or prevention of Alzheimer's disease.

Included within the aforementioned class of cyclohexane derivatives are cyclohexanones in which the carbon atom in the 4-position is bonded to an aryl or heteroaryl group and also to an arylsulphonyl or heteroarylsulphonyl group. Furthermore, said cyclohexanones are key intermediates in the synthesis of other members of the aforementioned class of cyclohexane derivatives, notably the corresponding 4,4-disubstituted cyclohexanepropanoic acids, and esters and amides derived therefrom. There is therefore a need for an efficient synthesis of said cyclohexanones and cyclohexanepropanoic acids, amenable to execution on a large scale.

According to the present invention, there is provided a method of preparing a cyclohexanone of formula (1):

(I)

comprising:
(a) cycloaddition of a 2-trialkylsilyloxybutadiene of formula (2a) to a vinyl derivative of formula (2b):

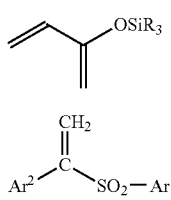

to form a silyl enol ether of formula (3):

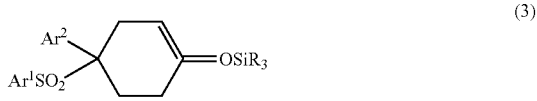

and
(b) hydrolysis of said silyl enol ether to form the cyclohexanone of formula (1);
wherein, in formulae (1), (2a), (2b) and (3), R represents $C_{1-6}$ alkyl;
$Ar^1$ represents $C_{6-10}$aryl or heteroaryl, either of which bears 0-3 substituents independently selected from halogen, CN, $NO_2$, $CF_3$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy; and
$Ar^2$ represents $C_{6-10}$aryl or heteroaryl, either of which bears 0-3 substituents independently selected from halogen, CN, $NO_2$, $CF_3$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy.

Each R independently represents an alkyl group of up to 6 carbon atoms, preferably up to 4 carbon atoms, such as methyl, ethyl, n-propyl, n-butyl and t-butyl. In a preferred embodiment, each R represents methyl.

Preferably, $Ar^1$ represents phenyl or heteroaryl, optionally substituted as indicated above. Typical heteroaryl embodiments of $Ar^1$ include optionally substituted pyridyl, in particular optionally substituted 3-pyridyl. Preferably, $Ar^1$ bears 0-2 substituents, more preferably 1 or 2 substituents, and most preferably 1 substituent which is preferably in the para-position relative to the sulphone group. Typical substituents include halogen (especially chlorine, bromine and fluorine), $C_{1-4}$alkyl (such as methyl), $C_{1-4}$alkoxy (such as methoxy), and $CF_3$. Examples of groups represented by $Ar^1$ include 4-chlorophenyl, 4-bromophenyl, 4-fluorophenyl, 4-trifluoromethylphenyl, 4-methylphenyl, 3,4-difluorophenyl, 3,4-dichlorophenyl, 4-methoxyphenyl, 6-trifluoromethylpyrid-3-yl and 6-chloropyrid-3-yl. Most preferably, $Ar^1$ represents 4-chlorophenyl, 4-trifluoromethylphenyl or 6-trifluoromethylpyrid-3-yl.

Preferably, $Ar^2$ represents phenyl bearing 1, 2 or 3 substituents as indicated, and most preferably, $Ar^2$ represents 2,5-disubstituted phenyl or 2,3,6-trisubstituted phenyl. Preferred substituents include halogen (especially bromine, chlorine and fluorine), nitrile and substituted alkyl, such as hydroxymethyl. Examples of groups represented by $Ar^2$ include 2,5-dichlorophenyl, 2,5-difluorophenyl, 2-bromo-5-fluorophenyl, 5-bromo-2-fluorophenyl, 5-iodo-2-fluorophenyl, 2-hydroxymethyl-5-fluorophenyl, 5-cyano-2-fluorophenyl and 2,3,6-trifluorophenyl. Most preferably, $Ar^2$ represents 2,5-difluorophenyl or 2,3,6-trifluorophenyl.

In a preferred embodiment, $Ar^1$ represents 4-chlorophenyl and $Ar^2$ represents 2,5-difluorophenyl.

In step (a), the cycloaddition reaction between the vinyl derivative (2b) and 2-trialkylsilyloxybutadiene (2a) to form silyl enol ether (3) may be carried out at elevated temperatures (e.g. 50-200° C., preferably 100-150° C.) in an inert solvent, especially a hydrocarbon solvent, preferably under an inert atmosphere. A preferred solvent is m-xylene. An excess of the 2-trialkylsilyloxybutadiene, e.g. of about 2-fold, may be used. In a typical procedure in accordance with the invention, the vinyl derivative (2b) is reacted with a 2-fold molar excess of 2-trimethylsilyloxybutadiene in m-xylene at 130° C. under nitrogen for a period of 5 to 50 hours, typically 10 to 30 hours, and preferably about 26 hours.

In step (b), the hydrolysis of the silyl enol ether (3) to the cyclohexanone (1) is typically carried out by treatment with aqueous mineral acid at ambient or moderately elevated temperature, e.g. in the range 20-100° C., preferably 30-80° C. Most advantageously, the hydrolysis is carried out in situ immediately after the cycloaddition reaction, without isolation or further purification of the silyl enol ether. In a typical procedure in accordance with the invention, the reaction mixture from step (a) is distilled under reduced pressure to remove residual diene with addition of solvent to maintain a constant volume, then diluted with THF and stirred vigorously with aqueous mineral acid (e.g. 3M hydrochloric acid) at about 50° C. The hydrolysis is typically complete within one hour at this temperature.

The product cyclohexanone (1) may then be isolated by separating the organic layer, washing it with water, and removing most of the solvent by distillation at atmospheric pressure. In a typical procedure, the residue from the distillation is allowed to cool to about 75° C., then heptane is added slowly to facilitate crystallisation of the product, which may then be collected and dried in the conventional manner.

The vinyl derivatives (2b) may be prepared from sulphones (4):

where $Ar^1$ and $Ar^2$ have the same meanings as before. For example, the sulphones (4) may be treated sequentially with butyllithium, trimethylsilyl chloride and formaldehyde in THF at −78° C. to form (2b). Alternatively, the aforesaid treatment with butyllithium may be followed by quenching with N,N-dimethylmethyleneammonium iodide and quaternisation of the resulting Mannich adduct with methyl iodide. Spontaneous elimination of trimethylamine during subsequent aqueous extractive work up then provides the vinyl derivatives (2b). However, in a preferred route to vinyl derivatives (2b), the sulphones (4) are reacted with N,N,N',N'-tetramethyldiaminomethane and acetic anhydride in DMF. In a typical process, the sulphone (4) is reacted with a 1.5- to 3-fold excess of the diamine and a 3- to 6-fold excess of acetic anhydride in DMF at about 60° C. for 4 to 18 hours, followed by cooling and dilution with water to precipitate the product.

The sulphones (4) are available via oxidation of the corresponding thioethers (5):

where $Ar^1$ and $Ar^2$ have the same meanings as before. A variety of oxidising agents may be used, such as hydrogen peroxide and peroxy acids, including m-chloroperoxybenzoic acid. In a preferred oxidative process, the thioether (5) is treated with hydrogen peroxide in a toluene-water biphasic system, in the presence of a sodium tungstate catalyst and a quaternary ammonium salt phase transfer catalyst, such as Aliquat 336™.

The thioethers (5) are available via reaction of thiols $Ar^1$—SH with $Ar^2$—$CH_2$—X, where $Ar^1$ and $Ar^2$ have the same meanings as before, and X is a leaving group, in particular halogen, preferably bromine or chlorine, or alkyl- or arylsulfonate such as mesylate, tosylate or triflate. The reaction takes place in the presence of base. In a preferred process, the reaction is carried out in industrial methylated spirits at ambient temperature or below, using aqueous sodium hydroxide as base.

In an alternative route to sulphones (4), $Ar^2$—$CH_2$—X is treated with a sulphinate salt $Ar^1SO_2Na$, where $Ar^1$, $Ar^2$ and X are as defined previously. The reaction takes place in DMF, and the product crystallises on addition of water.

The cyclohexanones (1) have utility as modulators of the processing of amyloid precursor protein by gamma secretase, and hence are potentially suitable for the treatment or prevention of Alzheimer's disease. Furthermore, chemical manipulation of the ketone group of the cyclohexanones (1) enables the synthesis of a variety of compounds showing similar or greater potency towards gamma secretase, providing access to drug candidates with varying pharmacokinetic profiles. In particular, the cyclohexanones are precursors of cyclohexanepropanoic acids (6) and esters and amides derived therefrom, which are disclosed in International Patent Application No. PCT/GB01/03741, filed 21 Aug. 2001, now published as WO 02/081435,

where $Ar^1$ and $Ar^2$ have the same meanings as before.

Accordingly, a preferred embodiment of the inventive process comprises the additional steps of:

(c) reacting a cyclohexanone of formula (1) with a di($C_{1-4}$alkyl) cyanomethylphosphonate and base to form a cyclohexylideneacetonitrile (7):

(d) reducing said cyclohexylideneacetonitrile with lithium tri-sec-butylborohydride to form the corresponding cis cyclohexaneacetonitrile (8):

(e) sequential treatment of said cis cyclohexaneacetonitrile with diisobutylaluminium hydride and aqueous acid to form the corresponding cis cyclohexaneacetaldehyde (9):

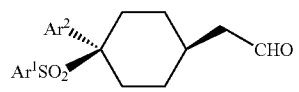

(f) homologation of said cis cyclohexaneacetaldehyde to the corresponding cis cyclohexanepropanal (10):

and (g) oxidising said cis cyclohexanepropanal to the corresponding cis cyclohexanepropanoic acid (6);

wherein, in each of steps (c) to (g), $Ar^1$ and $Ar^2$ have the same meanings as before, and "cis" refers to the stereoconfiguration of the side chain relative to the $Ar^1SO_2$ group.

In step (c), the $C_{1-4}$alkyl groups are typically methyl or ethyl, preferably ethyl, and the reaction is typically carried out in THF at 0° C. or below, e.g. at about −5° C., using a strong base such as potassium t-butoxide.

In step (d), the reduction is typically carried out in THF at about −60° C.

In step (e), the reaction with diisobutylaluminium hydride is typically carried out in toluene at about −40 to −60° C., and the subsequent acid hydrolysis by stirring the resulting solution with aqueous acid (e.g. citric acid) at ambient temperature for several hours (e.g. overnight). If desired, the aldehyde (9) may be isolated by evaporating the solvent and crystallising the residue (e.g. from aqueous DMF or from ethyl acetate and heptane). Alternatively, the toluene solution of aldehyde (9) may be used directly in the next step.

In one embodiment, the homologation in step (f) is effected by reaction of the cis cyclohexaneacetaldehyde (9) with a methoxymethyltriphenylphosphonium salt (e.g. a halide, such as the chloride) and strong base, followed by hydrolysis of the resulting mixture of enol ethers (11):

with aqueous acid. Typically, the reaction is carried out in toluene at reduced temperature (e.g. 0 to −60° C.) using potassium t-butoxide as the strong base. Typically, the phosphonium salt and the base are pre-reacted prior to addition of the aldehyde (9). The intermediate enol ether may be hydrolysed in its crude form in a mixture of aqueous hydrochloric acid and DMF at moderately elevated temperature (e.g. about 40-50° C.).

In an alternative embodiment, the homologation in step (f) is effected by reducing the cyclohexaneacetaldehyde (9) to the corresponding cyclohexaneethanol (for example, using sodium borohydride in an ethanol/toluene mixture at about 4° C.); converting same to a sulphonate ester such as the mesylate, tosylate or triflate (for example, by treatment with the appropriate sulphonyl chloride in dichloromethane in the presence of a tertiary amine at about −30° C.); displacing the sulphonate group with cyanide to form the corresponding cyclohexanepropionitrile (for example, using potassium cyanide in DMSO solution at ambient temperature); then treating said cyclohexanepropionitrile sequentially with diisobutylaluminium hydride and aqueous acid to form the desired aldehyde (10) (for example, under the same conditions as in step (e)).

In step (g), the oxidation is advantageously effected in a dichloromethane-water biphasic system at ambient temperature using an aqueous solution of sodium chlorite and sulphamic acid as oxidant.

Using conventional coupling reactions, the acids (6) may be converted to the corresponding esters and/or amides disclosed in International Patent Application No. PCT/GB01/03741, filed 21 Aug. 2001, now published as WO 02/081435. Alternatively, they may be converted to carboxylate salts by neutralisation with a suitable base, e.g. the sodium salt prepared by treatment with sodium hydroxide.

The above-described processes provide a convenient, economical route to the cyclohexanepropanoic acids of formula (6) which is suitable for execution on a multi-kilogram scale. Particularly noteworthy is the fact that the reduction in step (d) introduces the desired cis stereochemistry essentially quantitatively, thereby avoiding the need for a costly and time-consuming separation of cis and trans isomers.

Accordingly, the invention further provides a process for the synthesis of a cyclohexanepropanoic acid of formula (6) comprising the steps (c)-(g) detailed above.

The products of the novel processes disclosed herein have an activity as modulators of the processing of APP by γ secretase, and are therefore useful in the treatment or prevention of disorders involving excessive secretion and/or deposition of β-amyloid, in particular Alzheimer's disease.

For use in medicine, said products optionally may be in the form of pharmaceutically acceptable salts. Suitable pharmaceutically acceptable salts of the compounds made by the process of this invention include acid addition salts, such as those formed with hydrochloric, sulphuric, benzenesulphonic, methanesulphonic, fumaric, maleic, succinic, acetic, benzoic, oxalic, citric, tartaric, carbonic or phosphoric acids, and, where the compounds of the invention carry an acidic moiety, salts formed by neutralisation of said acidic moiety with a suitable base, such as sodium, potassium, ammonium, calcium or magnesium salts, and salts formed with suitable organic ligands, e.g. amine salts, quaternary ammonium salts or pyridinium salts.

The products formed via the inventive process may be used to prepare pharmaceutical compositions comprising one or more of the said products or pharmaceutically acceptable salts thereof and a pharmaceutically acceptable carrier. For use in said compositions, products of the inventive process which comprise a carboxylic acid group are preferably in the form of the free acid or the sodium salt thereof. Preferably these compositions are in unit dosage forms such as tablets, pills, capsules, powders, granules, sterile parenteral solutions or suspensions, metered aerosol or liquid sprays, drops, ampoules, transdermal patches, autoinjector devices or suppositories; for oral, parenteral, intranasal, sublingual or rectal administration, or for administration by inhalation or insufflation. For preparing solid compositions such as tablets, the principal active ingredient is mixed with a pharmaceutical carrier, such as the conventional tableting ingredients known to those skilled in the art, e.g. as described in WO 01/70677, and formed into unit dosage forms. Typical unit dosage forms contain from 1 to 250 mg, for example 1, 2, 5, 10, 25, 50, 100, 200 or 250 mg, of the active ingredient. Tablets or pills of the composition can be coated or otherwise compounded to provide a dosage form affording the advantage of prolonged action, as described, for example, in WO 01/70677.

The liquid forms in which the compositions may be incorporated for administration orally or by injection include aqueous solutions, suitably flavoured syrups, aqueous or oil suspensions, and flavoured emulsions with edible oils, as described in WO 01/70677.

For treating or preventing Alzheimer's disease, a suitable dosage level of the active ingredient is about 0.01 to 250 mg/kg per day, preferably about 0.05 to 100 mg/kg per day, and especially about 0.1 to 50 mg/kg of body weight per day. The compounds may be administered on a regimen of 1 to 4 times per day. In some cases, however, dosage outside these limits may be used.

Where the active ingredient is a carboxylic acid, it is preferably administered as the free acid or as the sodium salt thereof.

Assays for determining the level of activity of the relevant compounds towards γ-secretase are disclosed in WO 01/70677 and in *Biochemistry,* 2000, 39(30), 8698-8704. See also, *J. Neuroscience Methods,* 2000, 102, 61-68.

EXAMPLES

Example 1

2-[[(4-chlorophenyl)thio]methyl]-1,4-difluorobenzene

4-Chlorothiophenol (253 g, 1.75 mol) was dissolved in industrial methylated spirits (1265 mL) and 2M sodium hydroxide solution (901 mL) was added, maintaining the temperature below 20° C. A solution of 2,5-difluorobenzyl bromide (355 g, 1.72 mol) in industrial methylated spirits (250 mL) was added dropwise to the thiolate solution, maintaining the temperature below 15° C. Upon completion of the reaction, water (1000 mL) was added. The resulting slurry was aged at 5° C. and then filtered. The cake was washed sequentially with cold industrial methylated spirits: water (40:60) and then water (500 mL). Drying in vacuo at ambient temperature furnished 2-[[(4-chlorophenyl)thio]methyl]-1,4-difluorobenzene (462.3 g, 99.6%). $^1$H NMR (CDCl$_3$) 7.23 (4H, s), 6.69-6.86 (3H, m) and 4.04 (2H, s).

Example 2

2-[[(4-chlorophenyl)sulfonyl]methyl]-1,4-difluorobenzene

A mixture of sodium tungstate dihydrate (1.83 g, 5.54 mmol) as a solution in water (36.56 mL), 1M sulfuric acid (2.50 mL), 2-[[(4-chlorophenyl)thio]methyl]-1,4-difluorobenzene (Example 1) (100 g, 0.37 mol) and Aliquat 336™ (2.99 g, 7.39 mmol) in toluene (500 mL) was heated to 45° C., and 27.5% aqueous hydrogen peroxide (114.2 mL) was added slowly. The mixture was cooled and the unreacted peroxide was quenched by addition of 20 wt % sodium metabisulfite solution (120 mL). The layers were separated. The organic phase was washed with water (190 mL) and concentrated to a total volume of approximately 200 mL. Heptane (400 mL) was added and the resulting mixture was cooled to 0° C. and filtered. The wet cake was washed with 2:1 heptane:toluene (200 mL) and then heptane (200 mL). The product was dried in vacuo at 40° C. to yield 107.6 g of 2-[[(4-chlorophenyl)sulfonyl]methyl]-1,4-difluorobenzene (96% yield). $^1$H NMR CDCl$_3$ 7.61 (2H, d, J=8.6 Hz), 7.45 (2H, d, J=8.6 Hz), 7.13-7.08 (1H, m), 7.05-7.00 (1H, m), 6.99-6.87 (1H, m) and 4.36 (2H, s).

Example 3

2-[1-[(4-chlorophenyl)sulfonyl]ethenyl]-1,4-difluorobenzene

2-[[(4-chlorophenyl)sulfonyl]methyl]-1,4-difluorobenzene (Example 2) (100 g, 0.33 mol) and N,N,N',N'-tetramethyldiaminomethane (34.2 g, 0.50 mol) were dissolved in dimethyl formamide (1000 mL) at 60° C. Acetic anhydride (68.3 g, 1.00 mol) was added slowly and the reaction mixture was aged for 5 hours. Water (1000 mL) was added dropwise and the resulting slurry was cooled to 5° C. The solids were filtered, and the cake washed sequentially with dimethyl formamide:water (40:60, 200 mL) and water (500 mL). Drying overnight in vacuo at 40° C. under a nitrogen stream furnished 2-[1-[(4-chlorophenyl)sulfonyl]ethenyl]-1,4-difluorobenzene (98 g, 95%). $^1$H NMR (CDCl$_3$) 7.64-7.59 (2H, m), 7.43-7.39 (2H, m), 7.27-7.22 (1H, m), 7.08-6.88 (2H, m), 6.88 (1H, s) and 6.09 (1H, s).

Example 4

4-[(4-chlorophenyl)sulfonyl]-4-(2,5-difluorophenyl)cyclohexanone

A solution of 2-[1-[(4-chlorophenyl)sulfonyl]ethenyl]-1,4-difluorobenzene (Example 3) (100 g, 0.32 mol) in xylenes (500 ml) was azeotropically distilled at 38° C., 20 mmHg, until 300 mL solvent had been removed. 2-Trimethylsilyloxybutadiene (90.4 g, 0.64 mol) was then added under a nitrogen atmosphere and the mixture heated to 130° C. After the reaction was completed, the mixture was distilled in vacuo to remove residual diene, whilst maintaining a constant volume by the addition of xylenes (400 mL). The mixture was cooled to 50° C. and THF (500 mL) and 3M HCl (424 mL, 1.27 mol) were added. After the hydrolysis was complete, the layers were separated. The organic layer was washed with water (300 mL) and then concentrated by atmospheric distillation until 350 mL of solvent had been removed. The solution was allowed to cool until crystallisation started, heptane (600 mL) was added and the resulting mixture cooled to ambient. The solids were filtered and washed sequentially with heptane:xylenes (3:1, 200 ml) and then heptane (200 ml). Drying overnight in vacuo at 40° C. furnished 4-[(4-chlorophenyl)sulfonyl]-4-(2,5-difluorophenyl)cyclohexanone (110 g, 90% yield). $^1$H NMR CDCl$_3$ 7.43-7.37 (4H, m), 7.22-7.1 (2H, m), 6.97-6.9 (1H, m), 3.05-2.98 (4H, m) and 2.61-2.53 (4H, m).

Example 5

[4-[(4-chlorophenyl)sulfonyl]-4-(2,5-difluorophenyl)cyclohexylidene]-acetonitrile To a solution of potassium tert butoxide (1.0M in THF, 3.20 Kg, 3.55 mol) in tetrahydrofuran (2.1 L) was added diethyl (cyanomethyl)phosphonate (642 g, 3.62 mol), maintaining the temperature below 5° C. The resulting solution was aged for 2 h and a solution of 4-[(4-chlorophenyl)sulfonyl]-4-(2,5-difluorophenyl)cyclohexanone (1.07 Kg, 2.78 mol) (Example 4) in tetrahydrofuran (3.9 L) was added. After the reaction was completed, isopropyl acetate (13.1 L) and water (26.3 L) were added. The organic layer was washed with brine and then concentrated to 1 L. Heptane (10.5 L) was added. The resulting solid was filtered, washed with heptane, dried in vacuo at 37° C. and then slurried in diethyl ether (5 L). Filtration and drying in vacuo afforded 989 g (87% yield) of [4-[(4-chlorophenyl)sulfonyl]-4-(2,5-difluorophenyl)cyclohexylidene]acetonitrile. $^1$H NMR (CDCl$_3$) 7.41-7.34 (4H, m), 7.25-7.06 (2H, m), 6.94-6.87 (1H, m), 5.12 (1H, s), 3.05-3.03 (1H, m), 2.92-2.86 (2H, m), 2.54-2.50 (1H, m), and 2.30-2.03 (4H, m).

Example 6 cis-4-[(4-chlorolphenyl)sulfonyl]-4-(2,5-difluorophenyl)cyclohexaneacetonitrile

L-Selectride™ (1.0M in tetrahydrofuran, 100 g, 113 mmol) was cooled to −60° C. A solution of [4-[(4-chlorophenyl)sulfonyl]-4-(2,5-difluorophenyl)cyclohexylidene]acetonitrile (Example 5) (40 g, 98 mmol) in tetrahydrofuran (200 mL) was added over 90 minutes, maintaining the temperature at −60° C. The solution was aged for 60 minutes and then quenched, over 60 minutes, into a solution of sodium chloride (30 g) in water (160 mL) containing 46% sodium hydroxide (1.1 g) and aqueous hydrogen peroxide (27%) (50 mL) at −5° C. Sodium metabisulphite (11.9 g) in water (100 mL) was added and the resulting mixture was allowed to warm to 23° C. Further sodium metabisulphite (6.0 g) in water (50 mL) was added and solution aged for 10 minutes. The solution was diluted with isopropyl acetate (300 mL) and the aqueous layer removed. The organic layer was diluted with isopropyl acetate (254 mL) and washed with water (254 mL). The organic layer was distilled to a volume of 150 mL as further isopropyl acetate (300 mL) was added. The solution was then reconcentrated to a final volume of 200 mL as heptane (500 mL) was introduced. After cooling to ambient, the resulting solids were filtered and washed with heptane (100 mL), dried under vacuum at 45° C. to afford cis-4-[(4-chlorophenyl)sulfonyl]-4-(2,5-difluorophenyl)cyclohexaneacetonitrile, (38.6 g, 94% yield). $^1$H NMR CDCl$_3$ 7.38-7.35 (2H, m), 7.32-7.29 (2H, m), 7.08-7.02 (2H, m), 6.86-6.80 (1H, m), 2.51 (2H, d, J=8 Hz), 2.42-2.45 (4H, m), 2.08-2.03 (1H, m), 1.93-1.86 (1H, m) and 1.70-1.61 (4H, m).

Example 7 cis-4-[(4-chlorophenyl)sulfonyl]-4-(2,5-difluorophenyl)cyclohexaneacetaldehyde

Method (1)
A solution of cis-4-[(4-chlorophenyl)sulfonyl]-4-(2,5-difluorophenyl)cyclohexaneacetonitrile (Example 6) (967.3 g, 2.36 mol) in toluene (15.8 L) and dichloromethane (4.85 L) was cooled to −63° C. and diisobutyl aluminium hydride (1.0M in toluene, 2.48 Kg, 2.89 mol) was added over 60 minutes. Stirring was continued at −60° C. for a further 30 minutes before the solution was transferred into 0.75M citric acid (25 L). The bi-phasic mixture was stirred overnight at 20° C., the layers were separated and the organic layer was washed with 2M hydrochloric acid (15.8 L), 10% sodium bicarbonate (15.8 L) and water (15.8 L). After evaporation of the solvents, the residue was crystallised from EtOAc/heptane to afford cis-4-[(4-chlorophenyl)sulfonyl]-4-(2,5-difluorophenyl)cyclohexaneacetaldehyde (922 g; 95% yield). $^1$H NMR (CD$_2$Cl$_2$) 9.65 (1H, t, J=1.7 Hz), 7.32-7.20 (4H, m), 6.98-6.88 (2H, m), 6.85-6.72 (1H, m), 2.57-2.45 (2H, m), 2.45-2.10 (5H, m) and 1.68-1.35 (4H, m).

Method (2)
Cis-4-[(4-chlorophenyl)sulfonyl]-4-(2,5-difluorophenyl)cyclohexaneacetonitrile (Example 6) (6.00 kg, 13.0 mol) was slurried in toluene (65.5 Kg) and cooled to approximately −45° C. Diisobutylaluminium hydride (1.0 M in toluene, 15.0 L, 15 mol) was added maintaining the temperature at −40° C. The solution was aged for 60 min at −40° C. and then MeOH (2.4 L) was added such that the temperature remained below −35° C. The resulting solution was allowed to warm to −10° C. then added to a citric acid solution (14.4 Kg in 66 Kg water). Toluene (5.3 Kg) was used to rinse. The biphasic mixture was aged overnight and then the layers separated. The organic layer was washed with a solution of NaHCO$_3$ (6.35 Kg) in water (83 Kg) and then with water (59 Kg). The toluene solution was concentrated to approximately 40 L and then filtered and diluted to a final volume of approximately 120 L with further toluene (69.2 Kg). The assay yield was 5.127 Kg (96%). This solution was held overnight before concentrating to a final volume of 24.5 L.

Example 8 cis-4-[(4-chlorophenyl)sulfonyl]-4-(2,5-difluorophenyl)cyclohexanepropanal

Methoxymethyltriphenylphosphonium chloride (6.599 Kg, 19.3 mol) was slurried in THF (29.7 Kg) and cooled to −60° C. KO$^t$Bu (16.2 Kg, 18.0 mol) was then added such that the internal temperature did not exceed −30° C. Cis-4-[(4-chlorophenyl)sulfonyl]-4-(2,5-difluorophenyl)cyclohexaneacetaldehyde (Example 7) (5.127 Kg in toluene, total volume 24.5 L) was then added over 20 min maintaining the internal temperature below −20° C. Further toluene (1 L) was used to rinse. The mixture was aged for 30 min at below −20° C. before warming to ambient temperature and stirring for 2.0 hr. Acetic acid (0.35 Kg) was added followed by water (50.3 Kg). The layers were separated and the organic layer washed with brine. The volume was reduced to 22 L under vacuum, then DMF (53.5 Kg) was added and the mixture reconcentrated under vacuum to a final volume of ca. 61 L. A mixture of conc. HCl (1.22 Kg) and water (9.3 Kg) was then added and the mixture heated to 45° C. for 2 hr. After cooling, H$_2$O (25.5 Kg) was added to crystallise the product. The solids were isolated by filtration and washed with a mixture of DMF and water (4.7 Kg and 5.0 Kg respectively), then water (2×15.0 Kg). The solids were then oven dried in vacuo at 50° C. to give cis-4-[(4-chlorophenyl)sulfonyl]-4-(2,5-difluorophenyl)cyclohexanepropanal (5.594 Kg, 87%). $^1$H NMR (CD$_2$Cl$_2$) 9.67 (1H, t, J=1.5 Hz), 7.32-7.20 (4H, m), 7.03-6.90 (2H, m), 6.82-6.70 (1H, m), 2.39-2.22 (6H, m), 1.72-1.51 (4H, m) and 1.50-1.30 (3H, m).

Example 9 cis-4-[(4-chlorophenyl)sulfonyl]-4-(2,5-difluorophenyl)cyclohexanepropanal (Alternative Route)
(i). Sodium borohydride (97.9 g, 2.59 mol) was added to a solution of cis-4-[(4-chlorophenyl)sulfonyl]-4-(2,5-difluorophenyl)-cyclohexaneacetaldehyde (922 g, 2.24 mol) (Example 7) in absolute ethanol (6.3 L) and toluene (500 mL). The reaction was stirred at 4° C. for 60 minutes before hydrochloric acid (2M, 2.43 L) was added. The mixture was allowed to warm to 20° C. and stirred until a clear solution was obtained. The latter was transferred into tert-butyl methyl ether (15.8 L) and water (15.8 L), the layers were separated and the organic layer was washed with water (15.8

L). The solution was evaporated to dryness, and 2.4 L toluene was added to the residue. After the product crystallized, n-heptane (480 mL) was added. The slurry was filtered and washed with cold heptane (1 L). The solid was dried under vacuum at 38° C. to provide cis-4-[(4-chlorophenyl) sulfonyl]-4-(2,5-difluorophenyl)cyclohexaneethanol (650 g). Another 144 g was obtained via chromatography of the mother liquors on silica gel, eluting with 30% ethyl acetate in hexanes (combined yield 85%). $^1$H NMR CDCl$_3$ 7.37-7.30 (4H, m), 7.10-7.00 (2H, m), 6.86-6.79 (1H, m), 3.73-3.68 (2H, m), 2.42-2.36 (4H, m), 1.78-1.69 (5H, m) and 1.53-1.43 (2H, m).

(ii). A solution of cis-4-[(4-chlorophenyl)sulfonyl]-4-(2,5-difluorophenyl)cyclohexaneethanol (Step (i)) (790 g, 1.9 mol) in dichloromethane (7.9 L) was cooled to −25° C. and triethylamine (344 ml, 2.47 mol) was added followed by methanesulfonyl chloride (154 ml, 1.99 mol) whilst maintaining the temperature below −25° C. The reaction mixture was aged for 90 min. and then quenched into water (7.9 L). The layers of the resulting 2-phase mixture were separated. The organic layer was washed with brine (4 L), the brine layer extracted with dichloromethane (2 L), the combined organic layers dried over sodium sulfate and then concentrated to dryness. The residue was dissolved in dimethyl sulphoxide (7.9 L), and potassium cyanide (161 g, 2.47 mol) was added. The solution was stirred at ambient temperature for 16 hours, warmed to 30° C. for 3 hours, and then transferred into a mixture of isopropyl acetate (8 L) and water (16 L). Further isopropyl acetate (30 L) and water (30 L) were added. The layers were separated, and the combined organic layers were washed with water (8 L). The organic layer was concentrated to dryness, and the product purified by chromatography on silica gel, eluting with dichloromethane, to give cis-4-[(4-chlorophenyl)sulfonyl]-4-(2,5-difluorophenyl)cyclohexanepropionitrile (697 g, 87%). $^1$H NMR CDCl$_3$ 7.37-7.29 (4H, m), 7.09-7.00 (2H, m), 6.86-6.79 (1H, m), 2.47-2.37 (6H, m), 1.86-1.81 (2H, m), 1.78-1.72 (3H, m) and 1.61-1.52 (2H, m).

(iii). To a solution of cis-4-[(4-chlorophenyl)sulfonyl]-4-(2,5-difluorophenyl)cyclohexanepropionitrile (Step (ii)) (627 g, 1.48 mol) in dichloromethane (3.14 L) and toluene (10.19 L) at −60° C. under nitrogen was added 1.5M diisobutyl aluminium hydride (1.14 Kg, 2.0 mol) over 1 hour. The resulting solution was transferred into 0.75M citric acid solution (25 L), and the bi-phasic solution was stirred at room temperature overnight. The layers were separated and the organic phase was washed with 2M hydrochloric acid (17 L), water (20 L), and brine (1 L). Concentration to dryness provided crude cis-4-[(4-chlorophenyl)sulfonyl]-4-(2,5-difluorophenyl)cyclohexanepropanal as a white solid. $^1$H NMR CDCl$_3$—as for Example 8

Example 10 cis-4-[(4-chlorophenyl)sulfonyl]-4-(2,5-difluorophenyl)cyclohexanepropanoic acid To a solution of crude cis-4-[(4-chlorophenyl)sulfonyl]-4-(2,5-difluorophenyl)cyclohexanepropanal (Example 9) (650 g, 1.52 mol) in CH$_2$Cl$_2$ (6 L) and H$_2$O (6 L) was added sulfamic acid (215.5 g, 2.21 mol) followed by slow addition of sodium chlorite (180 g in 3.13 L H$_2$O, 2.0 mol) over 30 min. maintaining the internal temperature below 30° C. The phases were separated and the organic layer was washed with an aqueous Na$_2$S$_2$O$_5$ solution (157 g in 20 L H$_2$O), water (20 L) and then dried (Na$_2$SO$_4$). The solution was concentrated in vacuo and the residue was recrystalised from isopropyl acetate/heptane to afford cis-4-[(4-chlorophenyl) sulfonyl]-4-(2,5-difluorophenyl)cyclohexanepropanoic acid (482 g, 74%). $^1$H NMR (CDCl$_3$) 7.37-7.30 (4H, m), 7.09-6.99 (2H, m), 6.85-6.79 (1H, m), 2.42-2.36 (6H, m), 1.85-1.79 (2H, m), 1.73-1.69 (2H, m), 1.63-1.58 (1H, m) and 1.53-1.45 (2H, m).

Example 11

Sodium cis-4-[(4-chlorophenyl)sulfonyl]-4-(2,5-difluorophenyl)cyclohexanepropanoate Cis-4-[(4-chlorophenyl)sulfonyl]-4-(2,5-difluorophenyl) cyclohexane propanoic acid (Example 10) (3.072 Kg, 6.87 mol) was dissolved in isopropanol (48.2 Kg) by warming to 50° C. The resultant solution was filtered with the aid of further isopropanol (26.0 Kg). The batch was then reduced using vacuum to a volume of 60 L. 2M Sodium hydroxide (3.365 L, 6.73 mol) was then added in one portion. Further isopropanol was slowly added (48.2 Kg) as the resulting solution was distilled at atmospheric pressure to a final volume of 34 L. The reaction mixture was allowed to cool slowly to ambient (19° C.) overnight and then filtered. The filter cake was washed with isopropanol (4.8 Kg) and then dried for 24 hr at 50° C. in vacuo under a nitrogen stream to furnish sodium cis-4-[(4-chlorophenyl)sulfonyl]-4-(2,5-difluorophenyl)cyclohexanepropanoate (3.088 Kg, 96%). $^1$H NMR (d$_6$-DMSO) 7.60 (2H, m), 7.36 (2H, m), 7.30 (1H, m), 7.19-7.07 (2H, m), 2.40 (2H, bd, J=13.2 Hz), 2.21 (2H, bt, J=13.2 Hz), 1.89 (2H, t, J=8.3 Hz), 1.62 (2H, bd, J=13.2 Hz), 1.57 (2H, q, J=8.3 Hz), 1.57 (1H, m) and 1.29 (2H, bt, J=13.2 Hz).

The invention claimed is:

1. A method of preparing a cyclohexanone of formula (1):

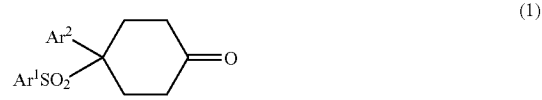

(1)

comprising:

(a) cycloaddition of a 2-trialkylsilyloxybutadiene of formula (2a) to a vinyl derivative of formula (2b):

(2a)

(2b)

to form a silyl enol ether of formula (3):

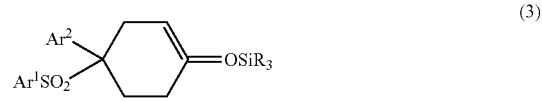

(3)

and
(b) hydrolysis of said silyl enol ether to form the cyclohexanone of formula (1);
wherein, in formulae (1), (2a), (2b) and (3), R represents $C_{1-6}$ alkyl;
$Ar^1$ represents $C_{6-10}$aryl or heteroaryl, either of which bears 0-3 substituents independently selected from halogen, CN, $NO_2$, $CF_3$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy; and
$Ar^2$ represents $C_{6-10}$aryl or heteroaryl, either of which bears 0-3 substituents independently selected from halogen, CN, $NO_2$, $CF_3$, OH, $OCF_3$, $C_{1-4}$alkoxy or $C_{1-4}$alkyl which optionally bears a substituent selected from halogen, CN, $NO_2$, $CF_3$, OH and $C_{1-4}$alkoxy.

2. A method according to claim 1 wherein the cycloaddition reaction between the vinyl derivative (2b) and 2-trialkylsilyloxybutadiene (2a) to form silyl enol ether (3) is carried out at 100-150° C. in a hydrocarbon solvent under an inert atmosphere.

3. A method according to claim 1 wherein hydrolysis of the silyl enol ether (3) to the cyclohexanone (1) is carried out in situ without isolation or further purification of the silyl enol ether.

4. A method according to claim 3 wherein said hydrolysis is carried out by treatment with aqueous mineral acid at 30-80□C.

5. A method according to claim 1 wherein each R represents methyl.

6. A method according to claim 1 wherein the vinyl derivative (2b) is prepared by reaction of a sulphone (4):

(4)

with N,N,N',N'-tetramethyldiaminomethane and acetic anhydride in DMF and $Ar^1$ and $Ar^2$ are as defined in claim 1.

7. A method of preparing cis-cyclohexanepropanoic acid of formula (6)

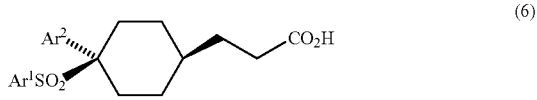

(6)

comprising the steps of:
(c) reacting a cyclohexanone of formula (1)

(1)

with a di($C_{1-4}$alkyl) cyanomethylphosphonate and base to form a cyclohexylideneacetonitrile (7):

(7)

(d) reducing said cyclohexylideneacetonitrile with lithium tri-sec-butylborohydride to form the corresponding cis cyclohexaneacetonitrile (8):

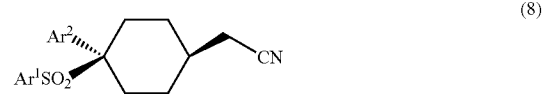

(8)

(e) sequential treatment of said cis cyclohexaneacetonitrile with diisobutylaluminium hydride and aqueous acid to form the corresponding cis cyclohexaneacetaldehyde (9):

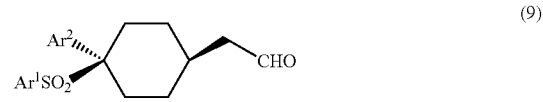

(9)

(f) homologation of said cis cyclohexaneacetaldehyde to the corresponding cis cyclohexanepropanal (10):

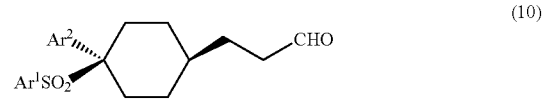

(10)

and
(g) oxidising said cis cyclohexanepropanal to the corresponding cis cyclohexanepropanoic acid (6);
wherein $Ar^1$ and $Ar^2$ are as defined in claim 1 and "cis" refers to the stereoconfiguration of the side chain relative to the $Ar^1SO_2$ group.

8. A method according to claim 7 wherein in step (c) the $C_{1-4}$ alkyl groups are ethyl, the reaction is carried out in THF at 0° C. or below and the base is potassium t-butoxide.

9. A method according to claim 7 wherein the reduction in step (d) is carried out in THF at about −60° C.

10. A method according to claim 7 wherein the homologation in step (f) is effected by reaction of the cis cyclohexaneacetaldehyde (9) with a methoxymethyltriphenylphosphonium salt and strong base, followed by hydrolysis of the resulting mixture of enol ethers with aqueous acid.

11. A method according to claim 7 comprising the additional step of neutralising the cyclohexanepropanoic acid (6) with sodium hydroxide to form the sodium salt thereof.

12. A method according to claim 1 wherein $Ar^1$ represents 4-chlorophenyl, 4-trifluoromethylphenyl or 6-trifluoromethylpyridin-3-yl and $Ar^2$ represents 2,5-difluorophenyl or 2,3,6-trifluorophenyl.

13. A method of preparing sodium cis-4-[(4-chlorophenyl)sulfonyl]-4-(2,5-difluorophenyl)cyclohexanepropanoate comprising the steps of:
(i) preparing 4-[(4-chlorophenyl)sulfonyl]-4-(2,5-difluorophenyl)cyclohexanone by the method of claim 1 wherein $Ar^1$ represents 4-chlorophenyl and $Ar^2$ represents 2,5-difluorophenyl;
(ii) reacting the product of step (i) with diethyl cyanomethylphosphonate and potassium tert-butoxide to form [4-[(4-chlorophenyl)sulfonyl]-4-(2,5-difluorophenyl)cyclohexylidene]-acetonitrile;

(iii) reducing the product of step (ii) with lithium tri-sec-butylborohydride to form cis-4-[(4-chlorophenyl)sulfonyl]-4-(2,5-difluorophenyl)cyclohexaneacetonitrile;

(iv) reacting the product of step (iii) sequentially with diisobutylaluminium hydride and with aqueous acid to form cis-4-[(4-chlorophenyl)sulfonyl]-4-(2,5-difluorophenyl)cyclohexanepropanal;

(v) reacting the product of step (iv) with methoxymethyltriphenyl-phosphonium chloride and potassium tert-butoxide, then hydrolysing the resulting mixture of enol ethers with aqueous acid to form cis-4-[(4-chlorophenyl)sulfonyl]-4-(2,5-difluorophenyl)cyclohexanepropanal;

(vi) oxidising the product of step (v) with aqueous sodium chlorite and sulphamic acid to form cis-4-[(4-chlorophenyl)sulfonyl]-4-(2,5-difluorophenyl)cyclohexanepropanoic acid; and (vii) neutralising the product of step (vi) with sodium hydroxide.

* * * * *